(12) United States Patent
Moszner et al.

(10) Patent No.: US 10,188,588 B2
(45) Date of Patent: Jan. 29, 2019

(54) ACIDIC HYBRID MONOMERS AND DENTAL MATERIALS BASED THEREON

(71) Applicant: Ivoclar Vivadent AG, Schaan (LI)

(72) Inventors: Norbert Moszner, Triesen (LI); Cederic Dellsperger, Mols (CH); Yohann Catel, Rans-Sevelen (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/455,195

(22) Filed: Mar. 10, 2017

(65) Prior Publication Data

US 2017/0281475 A1 Oct. 5, 2017

(30) Foreign Application Priority Data

Mar. 31, 2016 (EP) ..................................... 16163455

(51) Int. Cl.
*A61K 6/083* (2006.01)
*C08L 33/14* (2006.01)
(Continued)

(52) U.S. Cl.
CPC ............ *A61K 6/083* (2013.01); *A61K 6/0023* (2013.01); *A61K 6/0052* (2013.01); *A61K 6/087* (2013.01); *C07F 9/3808* (2013.01); *C07F 9/3826* (2013.01)

(58) Field of Classification Search
None
See application file for complete search history.

(56) References Cited

U.S. PATENT DOCUMENTS 6,512,068 B1 * 1/2003 Nakatsuka ............... C08L 33/08
526/274
6,900,251 B2 * 5/2005 Moszner ............... A61K 6/0023
522/171

(Continued)

FOREIGN PATENT DOCUMENTS

JP 2012006880 A 1/2012
JP 2015155396 A 8/2015
WO 200202057 A1 1/2002

OTHER PUBLICATIONS

Moad, Graeme et al., "Radical addition—fragmentation chemistry in polymer synthesis," ScienceDirect, Polymer 49, 2008, pp. 1079-1131, Elsevier.

(Continued)

*Primary Examiner* — Peter A Salamon
(74) *Attorney, Agent, or Firm* — Ann M. Knab; Thad McMurray

(57) ABSTRACT

Acidic monomer according to Formula I:

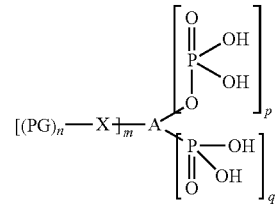

Formula I in which A is a linear or branched aliphatic $C_1$-$C_{18}$-hydrocarbon group, which can be interrupted by one or more —O—, —S—, —CO—O—, —O—CO—NH—, —HN—CO—NH— or —CO—NR$^1$—; R$^1$ is H or a $C_1$-$C_6$ alkyl (Continued)

group; X is absent or is a linear or branched aliphatic $C_1$-$C_{10}$ hydrocarbon group, which can be interrupted by one or more —O—, —S—, —CO—O—, —O—CO—NH—, —HN—CO—NH— or —CO—NR$^2$—; R$^2$ is H or a $C_1$-$C_6$ alkyl group; PG is a radically polymerizable group, preferably vinyl, allyl, $CH_2$=CR$^3$—CO—Y— or R$^4$O—CO—C(=CH$_2$)—CH$_2$—Y—; Y=O or NR$^5$ or is absent; R$^3$ is H or CH$_3$; R$^4$ is H or a $C_1$-$C_7$ alkyl group; R$^5$ is H or a $C_1$-$C_7$ alkyl group; n is 1, 2, 3 or 4; m=1 or 2; p=1, 2 or 3; and q=1, 2 or 3. The monomers are particularly suitable as components of dental material.

22 Claims, 1 Drawing Sheet

(51) Int. Cl.
*A61K 6/00* (2006.01)
*A61K 6/087* (2006.01)
*C07F 9/38* (2006.01)

(56) References Cited

U.S. PATENT DOCUMENTS

| | | | |
|---|---|---|---|
| 6,902,608 B2* | 6/2005 | Erdmann | C07F 9/3821 106/35 |
| 8,404,144 B2* | 3/2013 | Abuelyaman | A61K 6/0017 252/79.1 |
| 9,040,602 B2 | 5/2015 | Moszner et al. | |
| 2010/0076157 A1* | 3/2010 | Sekiguchi | A61K 6/0023 524/807 |
| 2012/0178720 A1* | 7/2012 | Arenz | A61K 31/663 514/108 |
| 2014/0296364 A1* | 10/2014 | Moszner | A61K 6/0023 522/171 |
| 2016/0145277 A1 | 5/2016 | Moszner | |
| 2016/0151249 A1 | 6/2016 | Moszner et al. | |

OTHER PUBLICATIONS

Jakubowski, W., et al., "Activators Regenerated by Electron Transfer for Atom-Transfer Radical Polymerization of (Meth)acrylates and Related Block Copolymers," Applied Chemistry, 2006, 118, pp. 4594-4598.

Kamigaito, M., et al., "Metal-Catalyzed Living Radical Polymerization," Chem. Rev. 2001, 101, pp. 3689-3745.

Catel, Y., et al., "Synthesis and evaluation of new phosphonic, bisphosphonic and difluoromethylphosphonic acid monomers for dental application," European Polymer Journal, 48 (2012) pp. 318-330.

* cited by examiner

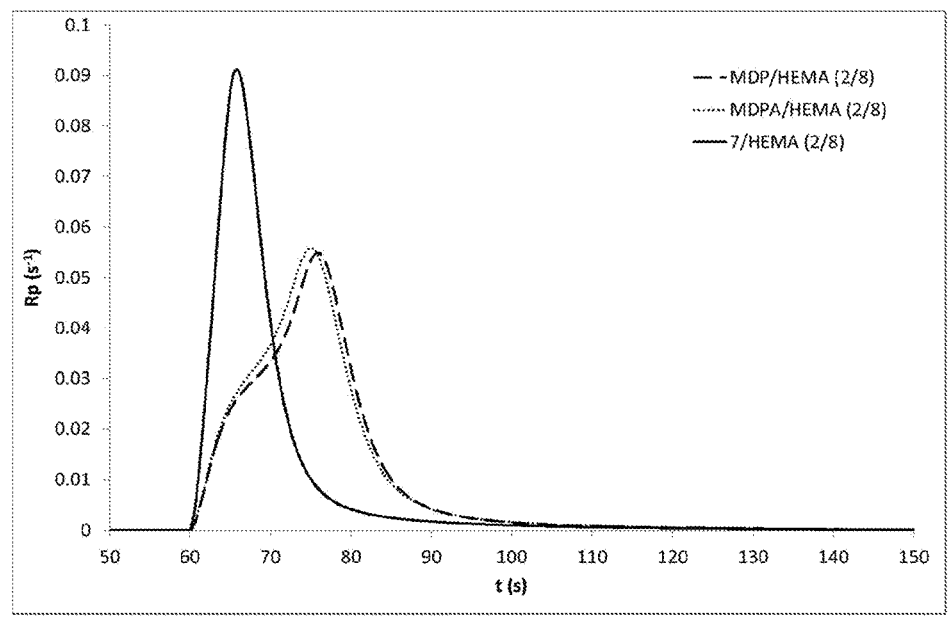

ACIDIC HYBRID MONOMERS AND DENTAL MATERIALS BASED THEREON

CROSS-REFERENCE TO RELATED APPLICATIONS

This application claims the benefit of European Patent Application No. 16163455.5 filed on Mar. 31, 2016, which is hereby incorporated by reference in its entirety.

TECHNICAL FIELD

The invention concerns monomers bearing one or more phosphonic acid groups and one or more dihydrogen phosphate groups which are able to undergo free-radical polymerization. The invention also relates to the use of such acidic monomers in dental materials such as adhesives, cements, composites and coating materials.

BACKGROUND

Acidic monomers, e.g. carboxylic, sulfonic, phosphonic acids and dihydrogen phosphates, are used in various kinds of dental materials, such as adhesives, self-adhesive resin cements or compomers. Self-etch adhesives (SEAs) are used to achieve a strong bond between restorative composites and the dental hard tissues (dentin and enamel). SEAs are aqueous solutions containing acidic monomers, cross-linking dimethacrylates, such as Bis-GMA (an addition product of methacrylic acid and bisphenol-A diglycidylether) or UDMA (an addition product of 2-hydroxyethyl methacrylate (HEMA) and 2,2,4-trimethylhexamethylenediisocyanate), monofunctional comonomers (e.g. HEMA), initiators and additives. The acidic monomer is the key component of SEAs as it is responsible for the etching of the dental hard tissues.

Self-adhesive resin cements (SARCs) adhere to both dentin and enamel without using an additional adhesive. Because of their simplicity of application, such materials have gained in popularity among dentists. SARCs comprise bulky crosslinking monomers (e.g., BisGMA or UDMA), diluents, such as triethylene glycol dimethacrylate (TEGDMA), an acidic monomer, different kinds of fillers, initiators and additives. In SARCs, acidic monomers are able to partially demineralize the dental hard tissues as well as to form a strong chemical adhesion with hydroxyapatite. Additionally, they can react with the filler to release fluoride ions.

Monomers bearing an acidic group (e.g. a phosphonic acid group) exhibit a high reactivity in free-radical polymerization. This phenomenon has been attributed to the ability of the acidic group to form strong hydrogen bonds. Acidic monomers commonly used in dental materials are, for example, 10-(methacryloyloxy)decyl dihydrogen phosphate (MDP), 2-(methacryloyloxy)ethyl dihydrogen phosphate (MEP), 4-[4-(methacryloyloxy)ethoxycarbonyl]phthalic acid (4-MET) or 2-[4-(dihydroxyphosphoryl)-2-oxa-butyl] acrylate (EAEPA).

EP 1 057 468 A1 and corresponding U.S. Pat. No. 6,512,068, which is hereby incorporated by reference, disclose dental adhesives containing polymerizable dihydrogen phosphates such as MDP. The use of polymerizable phosphonic acids in dental materials is, for example, described in EP 1 374 829 A1 and corresponding U.S. Pat. No. 6,900,251, which is hereby incorporated by reference, EP 1 169 996 A1 and corresponding U.S. Pat. No. 6,902,608, which is hereby incorporated by reference and WO 02/02057 A1.

The performance of SEAs and SARCs can be improved by incorporating acidic monomers exhibiting strong chelating properties. The use of β-ketophosphonic (EP 2 816 049 A1 and corresponding US 2016145277, which is hereby incorporated by reference,) and diphosphonic acids (WO 2004/060327 A1 and corresponding U.S. Pat. No. 8,404,144, which is hereby incorporated by reference, EP 2 755 624 A1 and corresponding U.S. Pat. No. 9,040,602, which is hereby incorporated by reference) in SEAs has been shown to result in a strong bond between a dental composite and the dental hard tissues.

Phosphonic acids bearing a urea group (EP 2 823 801 A1 and corresponding US 2016151249, which is hereby incorporated by reference,) were also able to significantly improve the adhesion of dental materials.

JP 2012-006880 A relates to dental adhesives containing hybrid acidic monomers bearing both a phosphonic and a carboxylic acid groups. US 2010/0076157 A1, which is hereby incorporated by reference, discloses the preparation of polymerizable dihydrogen phosphates comprising a carboxylic acid group and their use in dental materials.

SUMMARY

It is an object of the present invention to provide dental materials which form strong bonds to dental hard tissues (dentin and enamel), which show improved adhesive performance and improved reactivity compared to monomers comprising phosphonic acid groups or dihydrogen phosphate groups.

BRIEF DESCRIPTION OF THE DRAWINGS

Embodiments of the present invention will be more fully understood and appreciated by the following Detailed Description in conjunction with the accompanying drawings, in which:

FIG. 1 shows the rate of polymerization (Rp) versus irradiation time for the copolymerization of mixtures of monomers in accordance with an embodiment of the invention.

DETAILED DESCRIPTION

The invention is directed to dental materials comprising at least one acidic monomer according to the general formula I

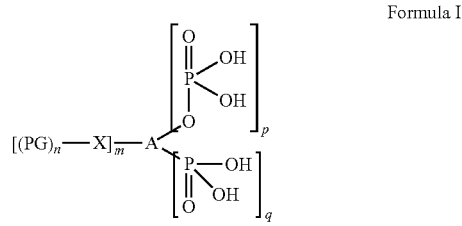

Formula I wherein
A=a linear or branched aliphatic $C_1$-$C_{18}$-hydrocarbon group, which can be interrupted by one or more —O—, —S—, —CO—O—, —O—CO—NH—, —HN—CO—NH— or —CO—NR$^1$—,
$R^1$=H or a $C_1$-$C_5$ alkyl group,
X=is absent or is a linear or branched aliphatic $C_1$-$C_{10}$ hydrocarbon group, which can be interrupted by one or more —O—, —S—, —CO—O—, —O—CO—NH—, —HN—CO—NH— or —CO—NR²—,
R²=H or a $C_1$-$C_6$ alkyl group,
PG=a radically polymerizable group, preferably vinyl, allyl, $CH_2$=$CR^3$—CO—Y— or $R^4$O—CO—C(=$CH_2$)—$CH_2$—Y—,
Y=O or $NR^5$ or is absent,
R³=H, $CH_3$, or
R⁴=H or a $C_1$-$C_7$ alkyl group,
R⁵=H or a $C_1$-$C_7$ alkyl group,
n=1, 2, 3 or 4,
m=1 or 2,
p=1, 2 or 3, and
q=1, 2 or 3.

The formula extends only to those compounds which are compatible with the theory of chemical valence. For example, if A is a $C_1$ radical, the sum of m, p and q can at most be 4. The indication that a radical is interrupted by one or more urethane groups, O atoms, S atoms etc. is to be understood to mean that these groups are inserted in each case into the carbon chain of the radical. These groups are thus bordered on both sides by C atoms and cannot be terminal. $C_1$ radicals cannot be interrupted. A sequence of hetero atoms and/or functional groups does not fall under this definition.

Formula I is to be understood to mean that m, p or q of the groups in brackets are bonded to the radical A. Preferably, the one or more polymerizable groups PG and the acidic groups are bound to opposite ends of the radical A. More preferably the one or more polymerizable groups PG on the one hand and the acid groups on the other hand are separated from each other by at least two, preferably at least three and more preferably at least 6 intermediate atoms. The intermediate atoms include the atom(s) to which the acidic groups —O—PO(OH)$_2$ and —PO(OH)$_2$ are bound.

Compounds of formula I in which the variables are defined as follows are preferred:
A=linear or branched $C_1$-$C_{10}$ aliphatic group, which can be interrupted by one or more —O—, —S—, —CO—O—, —O—CO—NH—, —HN—CO—NH— or —CO—NR¹—,
R¹=H,
X=—$CH_2$— or absent,
PG=$CH_2$=$CR^3$—CO—Y—,
Y=O or $NR^5$,
R³=H or $CH_3$,
R⁵=H or a $C_1$-$C_4$ alkyl group
n=1 or 2,
m=1,
p=1,
q=1.

Compounds of formula I in which the variables are defined as follows are particularly preferred:
A=linear or branched $C_3$-$C_{10}$ aliphatic group, which can be interrupted by one —O—, —S—, —CO—O—, —O—CO—NH—, —HN—CO—NH— or —CO—NR¹—,
R¹=H,
X=absent,
PG=$CH_2$=$CR^3$—CO—Y—,
Y=O or $NR^5$,
R³=H or $CH_3$,
R⁵=H or a $C_1$-$C_3$ alkyl group
n=1 or 2,
m=1,
p=1,
q=1.

In compounds according to formula I wherein p is 1 and q is 1 the dihydrogen phosphate group —O—PO(OH)$_2$ and the phosphonic acid group —PO(OH)$_2$ are preferably bound to the same carbon atom.

Acidic monomers of general formula I in which A is a $C_1$-$C_{18}$ aliphatic group, X is absent, PG=$CH_2$=$CCH_3$—CO—O—, n=1, m=1, p=1, q=1 and in which both the dihydrogen phosphate and the phosphonic acid groups are located on the same carbon atom can be prepared in 7 steps starting from the corresponding hydroxyalcanoic acid (Scheme 1). The alcohol group is first of all protected with the tert-butyldiphenylsilyl group. The reaction between the obtained carboxylic acid and oxalyl chloride leads to the desired acyl chloride. A subsequent reaction with triethylphosphite gives the corresponding α-ketophosphonate. The reaction of the α-ketophosphonate with diethylphosphite in the presence of a catalytic amount of diethylamine leads to the formation of a gem-phosphonate-phosphate compound. The deprotection of the tert-butyldiphenylsilyl group using tetrabutylammonium fluoride, followed by the acylation of the alcohol group with methacrylic anhydride, provides a gem-phosphonate-phosphate methacrylate. Finally, the deprotection of both phosphonate and phosphate groups is performed using bromotrimethylsilane followed by a methanolysis.

Scheme 1

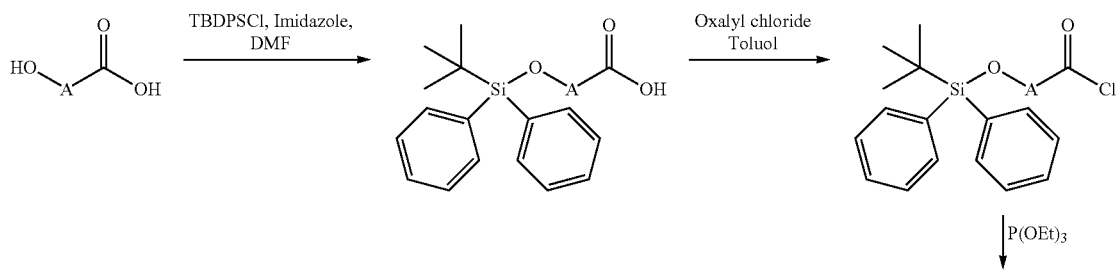

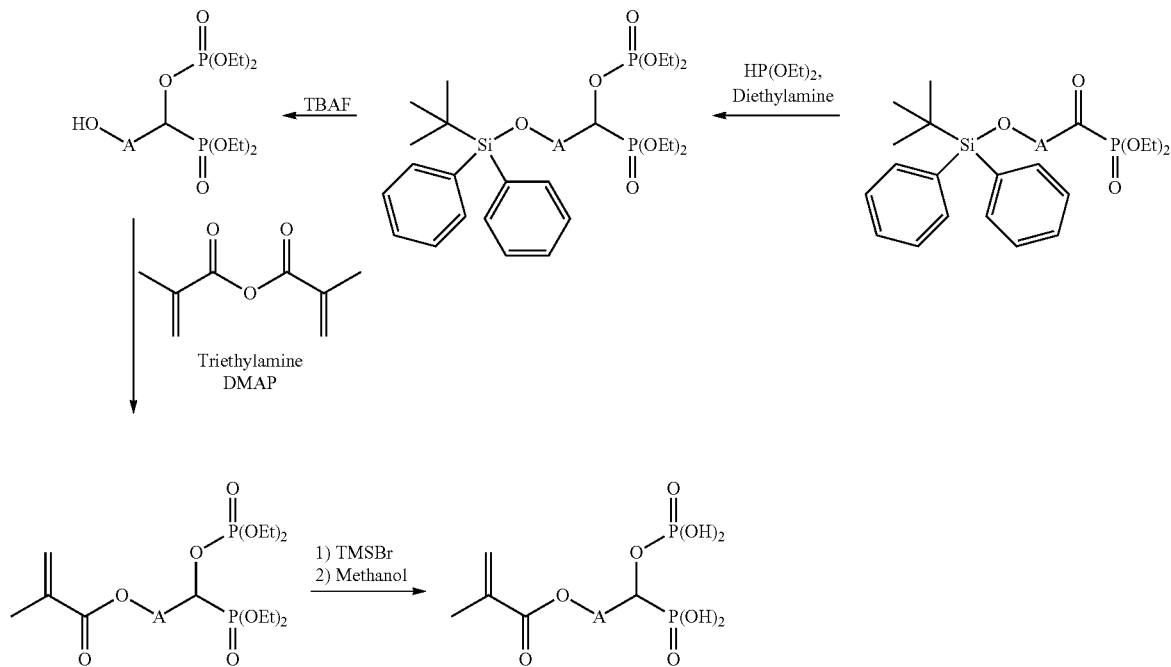

TBDPSCl=tert-butyldiphenylsilyl chloride; DMAP=4-dimethylaminopyridine, TBAF=tetrabutylammonium fluoride; TMSBr=bromotrimethylsilane Acidic monomers of general formula I in which A is a $C_1$-$C_{18}$ aliphatic group interrupted by a carbamate group, X is absent, PG=$CH_2$=$CCH_3$—CO—O—, n=1, m=1, p=1, q=1 and in which both the dihydrogen phosphate and the phosphonic acid groups are located on the same carbon atom can be prepared in 2 steps starting from a gem-phosphonate-phosphate bearing a hydroxyl group (Scheme 2). The reaction of such an alcohol ($R^a$ is a $C_1$-$C_{17}$ alkylene group) with an isocyanate bearing a methacrylate group ($R^b$ is a $C_1$-$C_{17}$ alkylene group chain), followed by the deprotection of both the diethyl phosphonate and diethyl phosphate groups, leads to the desired acidic hybrid monomer.

Scheme 2

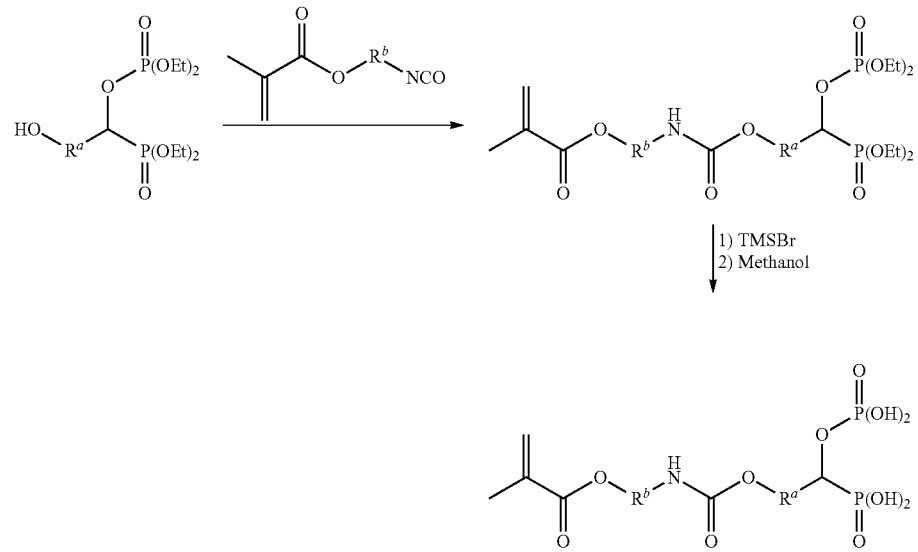

Preferred examples of the polymerizable acidic monomers of general formula I according to the invention are:
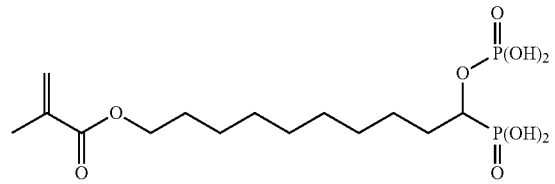
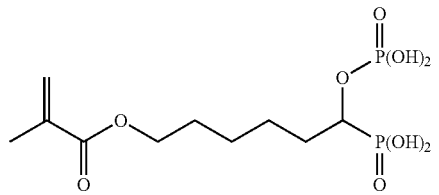
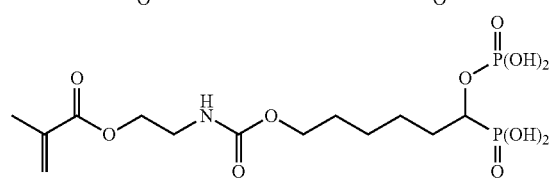
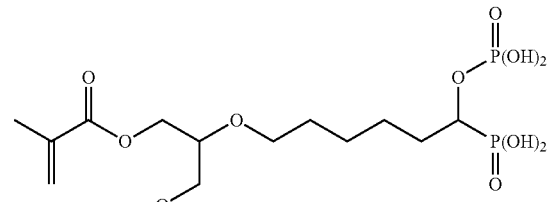
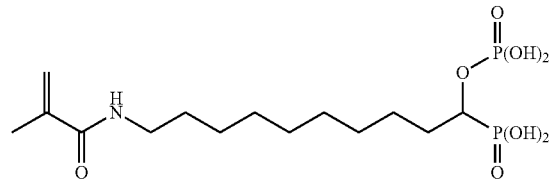
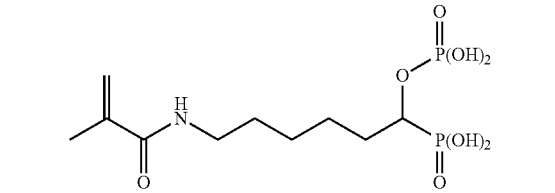
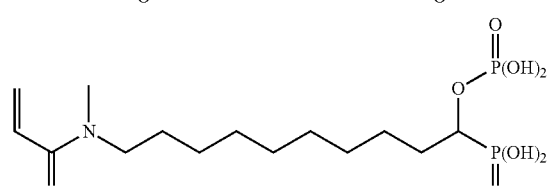
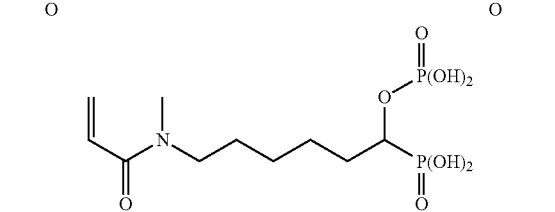
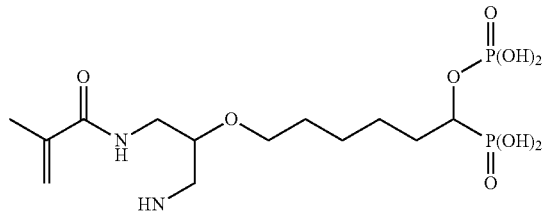
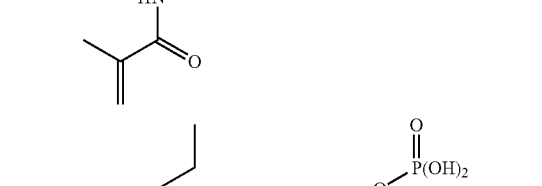
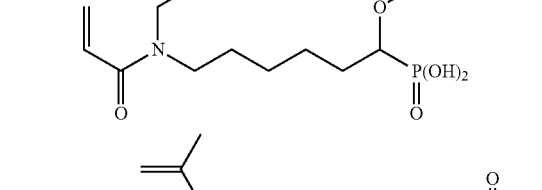
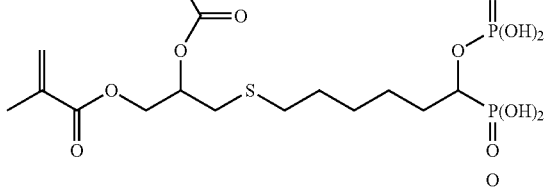
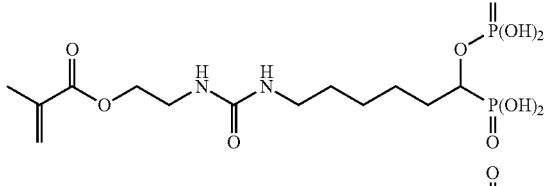
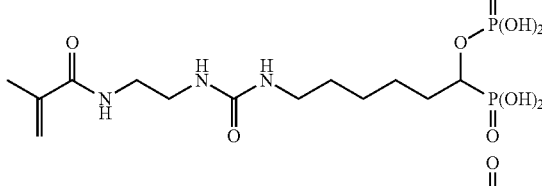
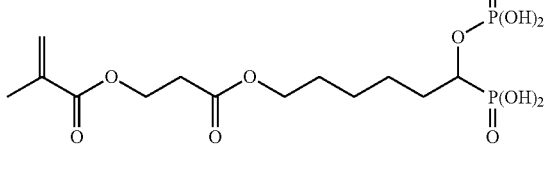
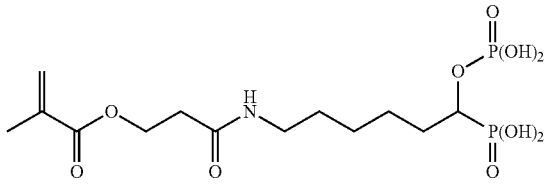
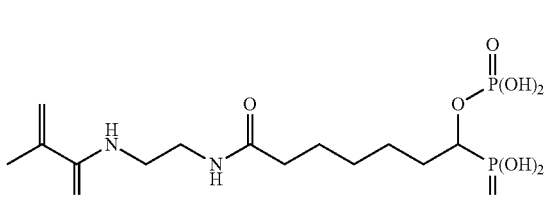

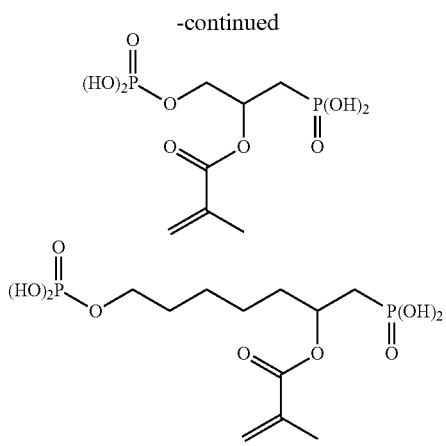

The polymerizable dihydrogen phosphate-phosphonic acid hybrid monomers of general formula I are particularly suitable for the preparation of dental materials, preferably self-etching dental materials.

The polymerizable dihydrogen phosphate-phosphonic acid hybrid monomers according to the present invention are readily soluble in alcohols, such as e.g. ethanol and isopropanol, and in acetone or in aqueous mixtures thereof. It was found that the monomers according to Formula I provide a better adhesion to both dentin and enamel in comparison with the corresponding phosphonic acids (same spacer length). In addition they are more reactive in free-radical polymerization than the corresponding polymerizable phosphonic acids or dihydrogen phosphates.

Dental materials according to the present invention preferably contain 0.1 to 50 wt.-% of at least one monomer according to Formula I, based on the total weight of the dental material, more preferably 1 and 20 wt.-%.

In addition to the acidic monomer(s) according to Formula I the dental materials according to the present invention preferably comprise at least one additional monomer (comonomer), which can undergo free radical polymerization. Preferred comonomers are mono- and multifunctional (meth)acrylates. Materials which contain at least one multifunctional (meth)acrylate or a mixtures of mono- and multifunctional (meth)acrylates as radically polymerizable monomer are particularly preferred. Monofunctional (meth)acrylates are monomers bearing only one polymerizable group whereas polyfunctional (meth)acrylates are bearing 2 or more (preferably 2 to 4) polymerizable groups. According to a quite particularly preferred embodiment, the compositions according to the invention contain at least one dimethacrylate or a mixture of mono- and dimethacrylates. Materials which contain mono- and multifunctional (meth) acrylates as radically polymerizable monomer are suitable in particular as dental materials, wherein methacrylates are preferred for materials which are cured intraorally.

Preferred (meth)acrylates are methyl, ethyl, hydroxyethyl, butyl, benzyl, tetrahydrofurfuryl or isobornyl (meth) acrylate, ethoxy- or propoxylated bisphenol A di(meth)acrylate, BisGMA, an addition product of methacrylic acid and bisphenol A diglycidyl ether, UDMA (an addition product of 2-hydroxyethyl methacrylate (HEMA) and 2,2,4-trimethylhexamethylene-diisocyanate), di-, tri- or tetraethylene glycol di(meth)acrylate, trimethylolpropane tri(meth) acrylate, pentaerythritol tetra(meth)acrylate and glycerol di(meth)acrylate, 1,4-butanediol di(meth)acrylate, 1,10-decanediol di(meth)acrylate and 1,12-dodecanediol di(meth) acrylate.

Another group of preferred comonomers are N-mono- or N-disubstituted acrylamides, such as e.g. N-ethylacrylamide, N,N-dimethylacrylamide, N-(2-hydroxyethyl)acrylamide, N-methyl-N-(2-hydroxyethyl)acrylamide, or N-monosubstituted methacrylamides, such as e.g. N-ethylmethacrylamide or N-(2-hydroxyethyl)acrylamide, and N-vinylpyrrolidone or allyl ether. These monomers are characterized by a high stability to hydrolysis and a relatively low viscosity and are therefore suitable, for example, as diluting monomers.

Comonomers, which are likewise preferred are crosslinking pyrrolidones, such as e.g. 1,6-bis(3-vinyl-2-pyrrolidonyl)hexane, or commercially available bisacrylamides, such as methylene- or ethylenebisacrylamide, or bis(meth)acrylamides, such as e.g. N,N'-diethyl-1,3-bis(acrylamido)propane, 1,3-bis(methacrylamido)propane, 1,4-bis(acrylamido) butane or 1,4-bis(acryloyl)piperazine, which can be synthesized by reaction of the corresponding diamines with (meth)acryloyl chloride. These monomers are also characterized by a high stability to hydrolysis. They contain two or more groups which can undergo free radical polymerization and are therefore suitable as crosslinking monomers.

Mixtures of one or more of the above mentioned monomers with further adhesive monomers, which contain an acidic group and can undergo free radical polymerization (acidic comonomers) can also be used.

Suitable comonomers containing an acidic group are polymerizable carboxylic acids, such as maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxy-propyl)-N-phenylglycine or 4-vinylbenzoic acid. Examples of suitable phosphonic acid monomers are vinylphosphonic acid, 4-vinylphenylphosphonic acid, 4-vinylbenzylphosphonic acid, 2-methacryloyloxyethylphosphonic acid, 2-methacrylamido-ethylphosphonic acid, 4-methacrylamido-4-methylpentyl-phosphonic acid, 2-[4-(dihydroxyphosphoryl)-2-oxabutyl]acrylic acid or 2-[4-(dihydroxyphosphoryl)-2-oxabutyl]acrylic acid ethyl or 2,4,6-trimethylphenyl ester. Examples of suitable polymerizable mono- or dihydrogen phosphates are 2-methacryloyloxypropyl mono- or dihydrogen phosphate, 2-methacryloyloxyethyl mono- or dihydrogen phosphate, 2-methacryloyloxyethyl phenyl hydrogen phosphate, dipentaerythritol pentamethacryloyloxyphosphate, 10-methacryloyloxydecyl dihydrogen phosphate, phosphoric acid mono-(1-acryloylpiperidin-4-yl) ester, 6-(methacrylamido)hexyl dihydrogen phosphate and 1,3-bis(N-acryloyl-N-propylamino)propan-2-yl dihydrogen phosphate. Examples of suitable polymerizable sulphonic acids are vinylsulphonic acid, 4-vinylphenylsulphonic acid or 3-(methacrylamido) propylsulphonic acid. The total amount of further monomers containing acid groups is preferably chosen such that it does not exceed the amount of monomers according to Formula I. Preferably the amount of acidic comomoners is lower than the amount of acidic monomers according to Formula I and more preferably the dental materials according to the present invention do not contain acidic comonomers.

The dental materials according to the present invention can also contain polymerizable acidic polymers. 'Polymerizable acidic polymer' refers to any kind of polymer, which comprises at least one acidic group and at least one radically polymerizable group. Preferred acidic groups are carboxylic, phosphonic, sulfonic acid groups and dihydrogen phosphate groups. Preferred radically polymerizable groups are (meth)acrylate, (N-alkyl)acrylamide and (meth)acrylamide groups. Such polymers can be synthesized, for example, by the reaction of a polycarboxylic acid with 2-isocyanatoethyl methacrylate or glycidyl methacrylate.

RAFT (Reversible Addition-Fragmentation chain Transfer) agents can also be incorporated into the dental materials according to the present invention. Examples of suitable RAFT agents are reported in the following review: Moad, G., Rizzardo, E., Thang, S. H. *Polymer* 2008, 49, 1079-1131. Preferred chain transfer agents are dithioesters, trithiocarbonates, allyl sulfide, allyl sulfones, and vinyl sulfoneesters.

Dental materials according to the present invention preferably also contain an initiator for the radical polymerization.

For the photopolymerization, initiators which comprise one component, two components or multiple components can be used. Norrish type I photoinitiators are particularly suitable. Benzoin and derivatives thereof as well as acyl- or bisacylphosphine oxides such as 2,4,6-trimethylbenzoyldiphenylphosphine oxide (Lucirin® TPO, BASF) or bis(2,4, 6-trimethylbenzoyl)phenylphosphine oxide (Irgacure® 818, BASF) can preferably be used as photoinitiators. Monoacyltrialkyl-, diacyldialkyl- or tetraacylgermanium compounds, such as e.g. benzoyltrimethylgermanium, dibenzoyldiethylgermanium, bis(4-methoxybenzoyl)diethylgermanium or tetrabenzoylgermanium are also preferred.

Other preferred photoinitiators are benzophenone and derivatives thereof as well as α-diketones or derivatives thereof, such as camphorquinone, 2,2-dimethoxy-2-phenylacetophenone, 1-phenylpropane-1,2-dione, diacetyl or 4,4'-dichlorobenzil, as well as coumarins and thioxanthones and their derivatives. These photoinitiators are preferably used in combination with a coinitiator. Preferred coinitiators are aliphatic and aromatic amines. Preferred aromatic amines are 4-(dimethylamino)benzoic acid esters, N,N-Dimethylamino-p-benzaldehyde, 4-(dimethylamino)benzonitrile, N,N,3,5-tetramethylaniline or N,N-dimethyl-p-toluidine. Preferred aliphatic amines are tertiary amines such as triethanolamine and N,N-dimethylaminoethyl methacrylate. Heterocyclic amines like 1,2,2,6,6-pentamethylpiperidine are also suitable. Amino acids such as N-phenylglycine can also be used. Other suitable coinitiators are silanes, e.g. tris(trimethylsilyl)silane, borane complexes and germanes.

Among the multicomponent photoinitiating systems, the combination ketone/amine/onium salt is the most preferred. As an example, iodonium salts such as e.g. diphenyliodonium hexafluorophosphate can be used in combination with camphorquinone and an amine. Mixtures of the various photoinitiators, such as e.g. dibenzoyldiethylgermanium in combination with camphorquinone and 4-dimethylaminobenzoic acid ethyl ester, can also be used.

Initiators which are preferably used for a polymerization carried out at room temperature are redox initiator combinations, such as e.g. combinations of benzoyl peroxide with N,N,3,5-tetramethylaniline, N,N-dimethyl-p-toluidine, N,N-diethyl-3,5-di-tert-butylaniline or N,N-diethanol-p-toluidine. Redox systems comprising peroxides or hydroperoxides and reducing agents, such as e.g. ascorbic acid, barbiturates, thioureas or sulphinic acids, are particularly preferred. Similarly to the systems used for ARGET ATRP, a combination of halogen compound (initiator)/transition metal/ligand/reducing agent can also be used to generate radicals (Jakubowski, W., Matyjaszewski, K. *Angew. Chem.* 2006, 118, 4594-4598; Kamigaito, M., Abdo, T., Sawamoto, M. *Chem. Rev.* 2001, 101, 3689-3745).

The dental materials according to the invention preferably comprise a photoinitiator or a combination of a photoinitiator and a redox initiator, preferably a peroxide. A particularly preferred initiator combination for the dual curing is a mixture of camphorquinone and benzoyl peroxide, wherein these initiators are also preferably combined with an amine.

The dental materials according to the present invention furthermore preferably also comprise at least one filler, preferably organic or inorganic filler particles, for improving the mechanical properties or for adjusting the viscosity. Fillers for adapting the mechanical properties preferably have an average particle diameter ranging from 10 nm to 10 µm, preferably from 10 nm to 1.0 µm, and fillers for adjusting the viscosity preferably from 10 to 1,000 nm, preferably from 10 to 200 nm. These filler types are preferably employed together. Unless stated otherwise, the average particle diameter is the weight-average value.

Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate or microfine fillers, such as pyrogenic silica or precipitated silica, and mini-fillers, such as quartz, glass ceramic or glass powder having an average particle diameter ranging from 0.01 to 1 µm, and radiopaque fillers, such as ytterbium fluoride or nanoparticulate tantalum(V) oxide or barium sulphate. Preferred organic fillers are fillers based on poly (meth)acrylates, such as e.g. PMMA, or cellulose derivatives, such as e.g. carboxymethylcellulose, which are ground to the abovementioned particle size after curing. The organic fillers can in turn have a filler content of the inorganic fillers mentioned.

To improve the bond between the filler particles and the crosslinked polymerization matrix, $SiO_2$-based fillers can be surface-modified with (meth)acrylate-functionalized silanes. An example of such silanes is 3-(meth)acryloyloxypropyltrimethoxysilane. To surface-modify non-silicate fillers, e.g. of $ZrO_2$ or $TiO_2$, functionalized acidic phosphates, such as e.g. 10-(meth)acryloyloxydecyl dihydrogen phosphate can also be used.

Solvent-containing dental materials represent a further preferred embodiment of the invention. Preferred solvents are water and polar organic solvents, such as acetone, isopropanol and, in particular, ethanol and mixtures of these solvents. Mixtures of water and polar organic solvents, in particular mixtures of water and ethanol, water and acetone or water, ethanol and acetone, are particularly preferred.

In addition, the dental materials according to the present invention can optionally comprise further additives, such as stabilizers, flavoring substances, colorants, microbicidal active compounds, additives which release fluoride ions, optical brighteners, plasticizers and/or UV absorbers.

Dental materials according to the invention which comprise the following components are particularly preferred:

a) 0.1 to 50 wt.-%, preferably 1 to 35 wt.-% and most preferably 1 to 20 wt.-% of acidic monomer(s) of general formula I, b) 0.01 to 10 wt.-%, preferably 0.1 to 3.0 wt.-% of initiator(s), c) 5 to 80 wt.-%, preferably 5 to 60 wt.-% of additional monomer(s), d) 0 to 80 wt.-% of filler(s), e) 0 to 70 wt.-%, preferably 0 to 50 wt.-% and most preferably 0 to 25 wt.-% of solvent(s), and optionally f) 0.01 to 10 wt.-%, preferably 0.01 to 3 wt.-% of further additive(s).

The amount of filler or fillers (d) depends on the intended use. Dental materials for use as adhesives preferably comprise 0 to 20 wt.-% and dental materials for use as cement or filling material (composite) preferably comprise 30 to 80 wt.-% of filler. Dental materials for use as cement or filling material preferably comprise no solvent.

Dental materials for use as adhesives preferably have the following composition:
a) 0.1 to 50 wt.-%, preferably 1 to 35 wt.-% and most preferably 1 to 20 wt.-% of acidic monomer(s) of general formula I,
b) 0.01 to 10 wt.-%, preferably 0.1 to 3.0 wt.-% of initiator(s),
c) 10 to 70 wt.-%, preferably 10 to 40 wt.-% of additional monomer(s),
d) 0 to 20 wt.-% of filler(s),
e) 5 to 50 wt.-%, preferably 5 to 40 wt.-% and most preferably 5 to 30 wt.-% of solvent(s), preferably water or a mixture of water, ethanol and/or acetone, and optionally
f) 0.01 to 3 wt.-% of further additive(s).

Dental materials for use as cements preferably have the following composition:
a) 0.1 to 50 wt.-%, preferably 1 to 35 wt.-% and most preferably 1 to 20 wt.-% of acidic monomer(s) of general formula I,
b) 0.01 to 10 wt.-%, preferably 0.1 to 3.0 wt.-% of initiator(s),
c) 10 to 70 wt.-%, preferably 10 to 40 wt.-% of additional monomer(s),
d) 30 to 75 wt.-% of filler(s),
e) 0 to 5 wt.-%, preferably less than 1 wt.-% of solvent(s),
f) 0.01 to 3 wt.-% of further additives.

All the percentages relate in each case to the total weight of the dental material.

Those materials in which the individual components are in each case chosen from the abovementioned preferred and particularly preferred substances are furthermore preferred.

The materials according to the invention are suitable in particular as dental materials, in particular as dental adhesives, cements, filling composites, veneering and coating materials.

The dental materials are suitable primarily for intraoral application by the dentist to restore damaged teeth (clinical materials), i.e. for therapeutic application, e.g. as dental cements, filling composites and veneering or blending materials. However, they can also be used extraorally, for example in the manufacture or repair of dental restorations, such as prostheses, artificial teeth, inlays, onlays, crowns and bridges (technical materials).

FIG. 1 shows the rate of polymerization (Rp) versus irradiation time for the copolymerization of mixtures of the monomer of Example 1 (according to the invention), MDP or MDPA with HEMA. FIG. 1 shows that the monomer of Example 1 is significantly more reactive than the known acidic monomers MDP and MDPA.

The following examples explain the invention in more detail.

EXAMPLES

Example 1

Synthesis of 10-methacryloyloxy-1-dihydroxyphosphoryloxy-decyl-phosphoric acid 7 a) Synthesis of 10-(tert-butyl-diphenylsilyloxy)decanoic acid 1

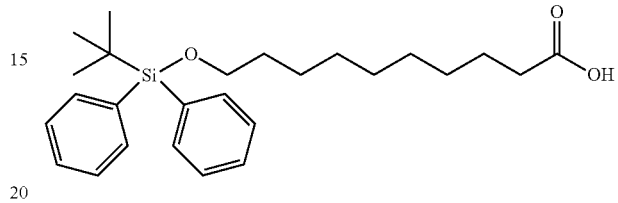

tert-Butylchlorodiphenylsilane (16.06 g, 58.4 mmol) was added, under argon atmosphere, to a solution of 10-hydroxydecanoic acid (10.0 g, 53.1 mmol) and imidazole (8.14 g, 119.5 mmol) in N,N-dimethylformamide (50 mL). The solution was stirred for 15 h at 50° C. The solution was poured into 200 mL of brine and the mixture was extracted with ethyl acetate (3*200 mL). The organic layers were gathered and washed with deionized water (2*300 mL). The organic layer was dried over sodium sulfate, filtrated and concentrated under reduced pressure. The crude product was purified by flash column chromatography (eluent=ethyl acetate/hexane: 2/8). 17.3 g of the desired carboxylic acid 1 were isolated as colorless oil. Yield=76%.

$^1$H NMR (400 MHz, CDCl$_3$): δ=1.05 (s, 9H, CH$_3$ tBu); 1.20-1.40 (m, 10H, CH$_2$); 1.50-1.69 (m, 4H, CH$_2$); 2.35 (t, $^3J_{HH}$=7.6 Hz, 2H, CH$_2$COOH); 3.65 (t, $^3J_{HH}$=6.5 Hz, 2H, CH$_2$OSi); 7.35-7.45 (m, 6H, CH$_{Ar}$); 7.65-7.70 (m, 4H, CH$_{Ar}$).

b) Synthesis of 10-(tert-butyl-diphenylsilyloxy)-decanoyl chloride 2

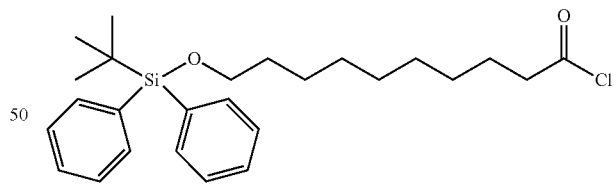

Oxalyl chloride (0.48 mL, 5.62 mmol) was added dropwise to a solution of carboxylic acid 1 (2.0 g, 4.69 mmol) in anhydrous toluene (15 mL). The solution was stirred for 4 h at room temperature. The solution was concentrated under reduced pressure. 2.09 g of colorless oil were obtained. Yield=100%.

$^1$H NMR (400 MHz, CDCl$_3$): δ=1.06 (s, 9H, CH$_3$ tBu); 1.22-1.40 (m, 10H, CH$_2$); 1.56 (qt, $^3J_{HH}$=6.8 Hz, 2H, CH$_2$); 1.71 (qt, $^3J_{HH}$=7.3 Hz, 2H, CH$_2$); 2.89 (t, $^3J_{HH}$=7.3 Hz, 2H, CH$_2$COCl); 3.66 (t, $^3J_{HH}$=6.5 Hz, 2H, CH$_2$OSi); 7.35-7.46 (m, 6H, CH$_{Ar}$); 7.65-7.71 (m, 4H, CH$_{Ar}$). $^{13}$C NMR (101 MHz, CDCl$_3$): δ=19.2 (SiC(CH$_3$)$_3$), 25.1 (CH$_2$); 25.7 (CH$_2$); 26.9 (CH$_3$); 28.4 (CH$_2$); 29.0 (CH$_2$); 29.2 (CH$_2$);

29.3 (CH$_2$); 32.5 (CH$_2$); 41.1 (CH$_2$COCl); 64.0 (CH$_2$OSi); 127.6 (C$_{Ar}$); 129.5 (C$_{Ar}$); 134.2 (C$_{Ar}$); 135.6 (C$_{Ar}$); 173.9 (COCl).

c) Synthesis of diethyl 10-(tert-butyl-diphenylsilyloxy)-1-oxo-decylphosphonate 3

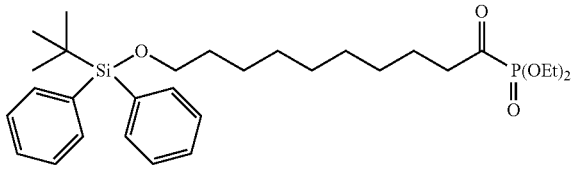

Triethylphosphite (0.81 mL, 4.72 mmol) was added dropwise, under argon atmosphere, at 0° C., to a solution of acyl chloride 2 (2.09 g, 4.69 mmol) in anhydrous dichloromethane (20 mL). The solution was stirred for 1 h at room temperature. The solution was concentrated under reduced pressure. 2.40 g of colorless oil were obtained. Yield=94%.

$^1$H NMR (400 MHz, CDCl$_3$): δ=1.04 (s, 9H, CH$_3$ tBu); 1.19-1.38 (m, 10H, CH$_2$); 1.37 (t, $^3J_{HH}$=7.1 Hz, 6H, POCH$_2$CH$_3$); 1.49-1.66 (m, 4H, CH$_2$); 2.83 (t, $^3J_{HH}$=7.3 Hz, 2H, CH$_2$COP); 3.64 (t, $^3J_{HH}$=6.5 Hz, 2H, CH$_2$OSi); 4.17-4.27 (m, 4H, POCH$_2$CH$_3$); 7.34-7.45 (m, 6H, CH$_{Ar}$); 7.64-7.69 (m, 4H, CH$_{Ar}$). $^{31}$P NMR (162 MHz, CDCl$_3$): δ=-2.7. $^{13}$C NMR (101 MHz, CDCl$_3$): δ=16.4 (d, $^3J_{CP}$=5.6 Hz, POCH$_2$CH$_3$); 19.2 (SiC(CH$_3$)$_3$), 22.4 (d, $^3J_{CP}$=3.8 Hz, CH$_2$CH$_2$COP); 25.8 (CH$_2$); 26.9 (SiC(CH$_3$)$_3$); 28.9 (CH$_2$); 29.2 (CH$_2$); 29.3 (CH$_2$); 29.4 (CH$_2$); 32.5 (CH$_2$); 43.4 (d, $^2J_{CP}$=53.8 Hz, CH$_2$COP); 63.7 (d, $^2J_{CP}$=7.3 Hz, POCH$_2$CH$_3$); 64.0 (CH$_2$OSi); 127.6 (C$_{Ar}$); 129.5 (C$_{Ar}$); 134.2 (C$_{Ar}$); 135.6 (C$_{Ar}$); 211.4 (d, $^1J_{CP}$=164.8 Hz, COP).

d) Synthesis of diethyl 10-(tert-butyl-diphenylsilyloxy)-1-diethoxyphosphoryloxy-decylphosphonate 4

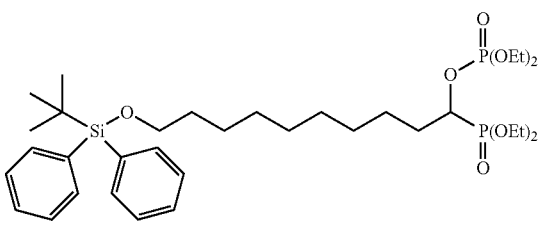

A solution of ketophosphonate 3 (15.4 g, 28.2 mmol) in diethyl ether (50 mL) was slowly added at 0° C. to a solution of diethyl phosphite (3.63 mL, 28.2 mmol) and diethylamine (2.92 mL, 28.2 mmol) in diethyl ether (80 mL). The reaction mixture was stirred for 30 min at 0° C. and for 24 h at room temperature. The solution was concentrated under reduced pressure. The crude product was purified by flash column chromatography (eluent=ethyl acetate). 16.1 g of the desired compound 4 were isolated as light yellow oil. Yield=83%.

$^1$H NMR (400 MHz, CDCl$_3$): δ=1.04 (s, 9H, CH$_3$ tBu); 1.19-1.66 (m, 26H, CH$_2$ and POCH$_2$CH$_3$); 1.76-1.98 (m, 2H, CH$_2$); 3.64 (t, $^3J_{HH}$=6.5 Hz, 2H, CH$_2$OSi); 4.07-4.26 (m, 8H, POCH$_2$CH$_3$); 4.57-4.69 (m, 1H, CHP); 7.33-7.46 (m, 6H, CH$_{Ar}$); 7.63-7.70 (m, 4H, CH$_{Ar}$). $^{31}$P NMR (162 MHz, CDCl$_3$): δ=-1.0 (d, $^3J_{PP}$=21.6 Hz, CHOP); 20.3 (d, $^3J_{PP}$=21.6 Hz, CHP). $^{13}$C NMR (101 MHz, CDCl$_3$): δ=16.0 (d, $^3J_{CP}$=4.4 Hz, POCH$_2$CH$_3$); 16.1 (d, $^3J_{CP}$=4.2 Hz, POCH$_2$CH$_3$); 16.4 (d, $^3J_{CP}$=5.8 Hz, POCH$_2$CH$_3$); 16.5 (d, $^3J_{CP}$=5.7 Hz, POCH$_2$CH$_3$); 19.2 (SiC(CH$_3$)$_3$); 25.4 (d, $^2J_{CP}$=10.7 Hz, CH$_2$CHP); 25.8 (CH$_2$); 26.9 (SiC(CH$_3$)$_3$); 29.3 (2C, CH$_2$); 29.4 (CH$_2$); 29.5 (CH$_2$); 31.0 (CH$_2$); 32.6 (CH$_2$); 62.8 (d, $^2J_{CP}$=6.6 Hz, POCH$_2$CH$_3$); 64.0 (d, $^2J_{CP}$=5.8 Hz, POCH$_2$CH$_3$); 64.0 (CH$_2$OSi); 73.2 (dd, $^1J_{CP}$=169.7 Hz, $^2J_{CP}$=7.4 Hz, CHP); 127.6 (C$_{Ar}$); 129.5 (C$_{Ar}$); 134.2 (C$_{Ar}$); 135.6 (C$_{Ar}$).

e) Synthesis of diethyl 10-hydroxy-1-diethoxyphosphoryloxy-decylphosphonate 5

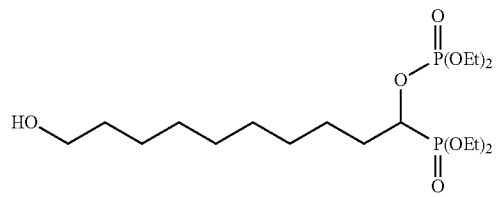

A solution of tetrabutyl ammonium fluoride (2.15 g, 6.82 mmol) in tetrahydrofuran (10 mL) was added dropwise to a solution of compound 4 (3.89 g, 5.68 mmol) in tetrahydrofuran (15 mL). The reaction mixture was stirred for 3 h at room temperature. A saturated solution of ammonium chloride (1 mL) was added. The solution was concentrated under reduced pressure. Deionized water (20 mL) was added and the solution was extracted with ethyl acetate (3*20 mL). The combined organic layers were dried over sodium sulfate and concentrated under reduced pressure. The crude product was purified by flash column chromatography (eluent=ethyl acetate/methanol: 9/1). 2.35 g of the desired alcohol 5 were isolated as colorless oil. Yield=93%.

$^1$H NMR (400 MHz, CDCl$_3$): δ=1.20-1.62 (m, 26H, CH$_2$ and POCH$_2$CH$_3$); 1.73-1.98 (m, 3H, CH$_2$ and OH); 3.59 (t, $^3J_{HH}$ 6.6 Hz, 2H, CH$_2$OH); 4.05-4.22 (m, 8H, POCH$_2$CH$_3$); 4.54-4.66 (m, 1H, CHP). $^{31}$P NMR (162 MHz, CDCl$_3$): δ=-1.1 (d, $^3J_{PP}$=21.8 Hz, CHOP); 20.2 (d, $^3J_{PP}$=21.8 Hz, CHP). $^{13}$C NMR (101 MHz, CDCl$_3$): δ=16.0 (d, $^3J_{CP}$=4.5 Hz, POCH$_2$CH$_3$); 16.1 (d, $^3J_{CP}$=4.4 Hz, POCH$_2$CH$_3$); 16.4 (d, $^3J_{CP}$=5.8 Hz, POCH$_2$CH$_3$); 16.5 (d, $^3J_{CP}$=5.7 Hz, POCH$_2$CH$_3$); 25.3 (d, $^2J_{CP}$=10.6 Hz, CH$_2$CHP); 25.7 (CH$_2$); 29.1 (CH$_2$); 29.2 (CH$_2$); 29.3 (CH$_2$); 29.4 (CH$_2$); 30.9 (CH$_2$); 32.7 (CH$_2$); 62.8 (d, $^2J_{CP}$=6.2 Hz, POCH$_2$CH$_3$); 62.9 (CH$_2$OH); 64.0 (d, $^2J_{CP}$=6.1 Hz, POCH$_2$CH$_3$); 73.2 (dd, $^1J_{CP}$=169.8 Hz, $^2J_{CP}$=7.3 Hz, CHP).

f) Synthesis of diethyl 10-methacryloyloxy-1-diethoxyphosphoryloxy-decylphosphonate 6

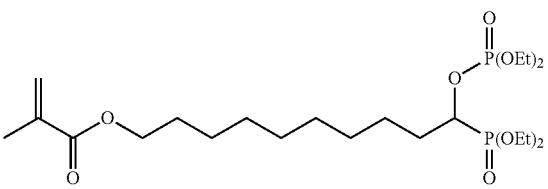

Methacrylic anhydride (1.15 mL, 7.73 mmol) was added, under argon atmosphere, to a solution of alcohol 5 (2.30 g, 5.15 mmol), 4-dimethylaminopyridine (31 mg, 0.26 mmol)

and triethylamine (1.08 mL, 7.73 mmol) in dry dichloromethane (20 mL). The reaction mixture was stirred for 6 h at room temperature. The solution was concentrated under reduced pressure. Ethyl acetate (50 mL) was added and the solution was washed with a saturated solution of sodium bicarbonate (2*50 mL). The combined organic layers were dried over sodium sulfate and concentrated under reduced pressure. The crude product was purified by flash column chromatography (eluent=ethyl acetate). 2.29 g of the desired monomer 6 were isolated as a colorless oil. Yield=86%.

$^1$H NMR (400 MHz, CDCl$_3$): δ=1.23-1.72 (m, 26H, CH$_2$ and POCH$_2$CH$_3$); 1.77-1.98 (m, 5H, CH$_2$ and CH$_3$); 4.08-4.25 (m, 10H, POCH$_2$CH$_3$ and CH$_2$OCO); 4.58-4.68 (m, 1H, CHP); 5.53-5.57 (m, 1H, CH$_2$=C); 6.10 (1s, 1H, CH$_2$=C). $^{31}$P NMR (162 MHz, CDCl$_3$): δ=−1.0 (d, $^3J_{PP}$=21.7 Hz, CHOP); 20.3 (d, $^3J_{PP}$=21.7 Hz, CHP). $^{13}$C NMR (101 MHz, CDCl$_3$): δ=16.0 (d, $^3J_{CP}$=4.4 Hz, POCH$_2$CH$_3$); 16.1 (d, $^3J_{CP}$=4.2 Hz, POCH$_2$CH$_3$); 16.4 (d, $^3J_{CP}$=5.7 Hz, POCH$_2$CH$_3$); 16.5 (d, $^3J_{CP}$=5.8 Hz, POCH$_2$CH$_3$); 18.3 (CH$_3$); 25.3 (d, $^2J_{CP}$=10.5 Hz, CH$_2$CHP); 26.0 (CH$_2$); 28.6 (CH$_2$); 29.2 (2C, CH$_2$); 29.3 (CH$_2$); 29.4 (CH$_2$); 31.0 (CH$_2$); 62.8 (d, $^2J_{CP}$=6.6 Hz, POCH$_2$CH$_3$); 64.0 (d, $^2J_{CP}$=5.9 Hz, POCH$_2$CH$_3$); 64.8 (CH$_2$OCO); 73.2 (dd, $^1J_{CP}$=169.6 Hz, $^2J_{CP}$=7.2 Hz, CHP); 125.2 (CH$_2$=C); 136.5 (CH$_2$=C); 167.6 (C=O).

g) Synthesis of 10-methacryloyloxy-1-dihydroxyphosphoryloxy-decylphosphonic acid 7

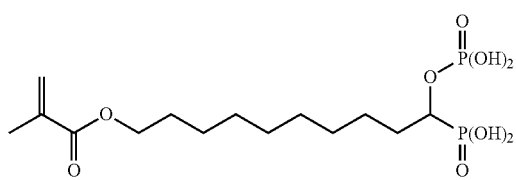

Bromotrimethylsilane (3.0 mL, 22.7 mmol) was added, under argon atmosphere, to a solution of monomer 6 (1.95 g, 3.79 mmol) in anhydrous dichloromethane (20 mL). After stirring for 5 h at 30° C., the mixture was concentrated under reduced pressure. Methanol (200 mL) was added and the mixture was stirred for 30 min at RT. The solvent was evaporated and the product was dried to a constant weight under vacuum. 1.52 g of the desired acidic monomer were isolated as a highly viscous yellow oil. Yield=100%.

$^1$H NMR (400 MHz, MeOD): δ=1.26-1.73 (m, 14H, CH$_2$); 1.75-1.96 (m, 5H, CH$_2$ and CH$_3$); 4.13 (t, $^3J_{HH}$=6.6 Hz, 2H, CH$_2$OCO); 4.35-4.46 (m, 1H, CHP); 5.59-5.62 (m, 1H, CH$_2$=C); 6.07 (1s, 1H, CH$_2$=C). $^{31}$P NMR (162 MHz, MeOD): δ=0.3 (d, $^3J_{PP}$=18.7 Hz, CHOP); 19.5 (d, $^3J_{PP}$=18.7 Hz, CHP). $^{13}$C NMR (101 MHz, MeOD): δ=17.1 (CH$_3$); 25.1 (d, $^2J_{CP}$=10.4 Hz, CH$_2$CHP); 25.7 (CH$_2$); 28.3 (CH$_2$); 28.9 (CH$_2$); 29.0 (CH$_2$); 29.1 (CH$_2$); 29.2 (CH$_2$); 30.7 (CH$_2$); 64.6 (CH$_2$OCO); 73.2 (dd, $^1J_{CP}$=165.9 Hz, $^2J_{CP}$=7.2 Hz, CHP); 124.7 (CH$_2$=C); 136.5 (CH$_2$=C); 167.5 (C=O).

Example 2

Synthesis of 6-methacryloyloxy-1-dihydroxyphosphoryloxy-hexylphosphonic acid 14 a) Synthesis of 6-(tert-butyl-diphenylsilyloxy)hexanoic acid 8

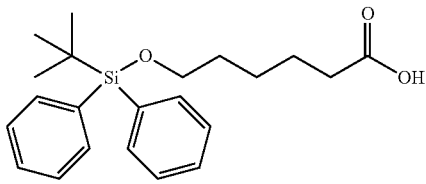 [SMILES: CC(C)(C)[Si](OCCCCCC(=O)O)(c1ccccc1)c1ccccc1]

6-(tert-butyl-diphenylsilyloxy)hexanoic acid 8 was synthesized, from 6-hydroxycaproic acid (25.0 g, 0.189 mol), according to the same procedure described for the synthesis of 10-(tert-butyl-diphenylsilyloxy)decanoic acid 1. 46.1 g of the desired carboxylic acid 8 were isolated as colorless oil. Yield=66%.

$^1$H NMR (400 MHz, CDCl$_3$): δ=1.04 (s, 9H, CH$_3$ tBu); 1.36-1.47 (m, 2H, CH$_2$); 1.52-1.67 (m, 4H, CH$_2$); 2.33 (t, $^3J_{HH}$=7.6 Hz, 2H, CH$_2$COOH); 3.65 (t, $^3J_{HH}$=6.4 Hz, 2H, CH$_2$OSi); 7.34-7.45 (m, 6H, CH$_{Ar}$); 7.63-7.69 (m, 4H, CH$_{Ar}$).

b) Synthesis of 6-(tert-butyl-diphenylsilyloxy)-hexanoyl chloride 9

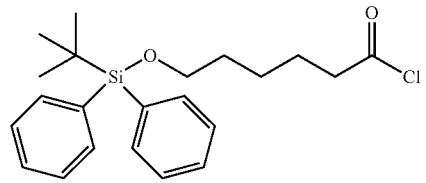 [SMILES: CC(C)(C)[Si](OCCCCCC(=O)Cl)(c1ccccc1)c1ccccc1]

6-(tert-butyl-diphenylsilyloxy)-hexanoyl chloride 9 was synthesized, from carboxylic acid 8 (10.0 g, 27.0 mmol), according to the same procedure described for the synthesis of 10-(tert-butyldiphenylsilyloxy)-decanoyl chloride 2. 10.5 g of the desired acyl chloride 9 were isolated as colorless oil. Yield=100%.

$^1$H NMR (400 MHz, CDCl$_3$): δ=1.05 (s, 9H, CH$_3$ tBu); 1.37-1.48 (m, 2H, CH$_2$); 1.51-1.61 (m, 2H, CH$_2$); 1.69 (qt, $^3J_{HH}$=7.6 Hz, 2H, CH$_2$); 2.86 (t, $^3J_{HH}$=7.4 Hz, 2H, CH$_2$COCl); 3.66 (t, $^3J_{HH}$=6.2 Hz, 2H, CH$_2$OSi); 7.35-7.46 (m, 6H, CH$_{Ar}$); 7.62-7.69 (m, 4H, CH$_{Ar}$).

c) Synthesis of diethyl 6-(tert-butyl-diphenylsilyloxy)-1-oxo-hexylphosphonate 10

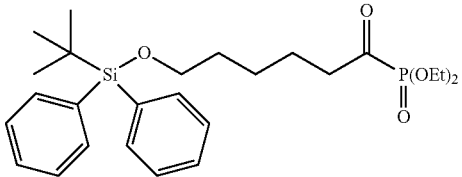

6-(tert-butyl-diphenylsilyloxy)-1-oxo-hexylphosphonate 10 was synthesized, from acyl chloride 9 (10.5 g, 26.9 mmol), according to the same procedure described for the synthesis of diethyl 10-(tert-butyl-diphenylsilyloxy)-1-oxo-decylphosphonate 3. 13.1 g of the desired α-ketophosphonate 10 were isolated as slightly yellow oil. Yield=100%.

$^1$H NMR (400 MHz, CDCl$_3$): δ=1.04 (s, 9H, CH$_3$ tBu); 1.32-1.44 (m, 2H, CH$_2$); 1.37 (t, $^3J_{HH}$=7.1 Hz, 6H, POCH$_2$CH$_3$); 1.50-1.67 (m, 4H, CH$_2$); 2.83 (t, $^3J_{HH}$=7.3 Hz, 2H, CH$_2$COP); 3.65 (t, $^3J_{HH}$=6.3 Hz, 2H, CH$_2$OSi); 4.17-4.27 (m, 4H, POCH$_2$CH$_3$); 7.33-7.46 (m, 6H, CH$_{Ar}$); 7.62-7.69 (m, 4H, CH$_{Ar}$). $^{31}$P NMR (162 MHz, CDCl$_3$): δ=-2.7. $^{13}$C NMR (101 MHz, CDCl$_3$): δ=16.4 (d, $^3J_{CP}$=5.6 Hz, POCH$_2$CH$_3$); 19.2 (SiC(CH$_3$)$_3$), 22.2 (d, $^3J_{CP}$=3.9 Hz, CH$_2$CH$_2$COP); 25.2 (CH$_2$); 26.9 (SiC(CH$_3$)$_3$); 32.2 (CH$_2$); 43.4 (d, $^2J_{CP}$=54.0 Hz, CH$_2$COP); 63.6 (CH$_2$OSi); 63.7 (d, $^2J_{CP}$=7.3 Hz, POCH$_2$CH$_3$); 127.6 (C$_{Ar}$); 129.6 (C$_{Ar}$); 134.0 (C$_{Ar}$); 135.6 (C$_{Ar}$); 211.2 (d, $^1J_{CP}$=165.2 Hz, COP).

d) Synthesis of diethyl 6-(tert-butyl-diphenylsilyloxy)-1-diethoxyphosphoryloxy-hexylphosphonate 11

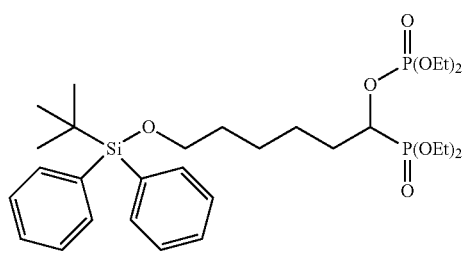

6-(tert-butyl-diphenylsilyloxy)-1-diethoxyphosphoryloxy-hexylphosphonate 11 was synthesized, from α-ketophosphonate 10 (13.1 g, 26.6 mmol), according to the same procedure described for the synthesis of diethyl 10-(tert-butyl-diphenylsilyloxy)-1-diethoxyphosphoryloxy-decylphosphonate 4. 12.0 g of the desired compound 11 were isolated as slightly yellow oil. Yield=72%.

$^1$H NMR (400 MHz, CDCl$_3$): δ=1.04 (s, 9H, CH$_3$ tBu); 1.26-1.66 (m, 18H, CH$_2$ and POCH$_2$CH$_3$); 1.76-1.99 (m, 2H, CH$_2$); 3.65 (t, $^3J_{HH}$=6.4 Hz, 2H, CH$_2$OSi); 4.05-4.25 (m, 8H, POCH$_2$CH$_3$); 4.56-4.68 (m, 1H, CHP); 7.34-7.45 (m, 6H, CH$_{Ar}$); 7.63-7.69 (m, 4H, CH$_{Ar}$). $^{31}$P NMR (162 MHz, CDCl$_3$): δ=-1.0 (d, $^3J_{PP}$=21.6 Hz, CHOP); 20.2 (d, $^3J_{PP}$=21.6 Hz, CHP). $^{13}$C NMR (101 MHz, CDCl$_3$): δ=16.0 (d, $^3J_{CP}$=3.4 Hz, POCH$_2$CH$_3$); 16.1 (d, $^3J_{CP}$=3.2 Hz, POCH$_2$CH$_3$); 16.4 (d, $^3J_{CP}$=5.6 Hz, POCH$_2$CH$_3$); 16.5 (d, $^3J_{CP}$=5.6 Hz, POCH$_2$CH$_3$); 19.2 (SiC(CH$_3$)$_3$) 25.3 (d, $^2J_{CP}$=10.5 Hz, CH$_2$CHP); 25.6 (CH$_2$); 26.9 (SiC(CH$_3$)$_3$); 31.0 (CH$_2$); 32.4 (CH$_2$); 62.8 (d, $^2J_{CP}$=6.6 Hz, POCH$_2$CH$_3$); 63.8 (CH$_2$OSi); 64.0 (d, $^2J_{CP}$=5.9 Hz, POCH$_2$CH$_3$); 73.2 (dd, $^1J_{CP}$=169.5 Hz, $^2J_{CP}$=7.2 Hz, CHP); 127.6 (C$_{Ar}$); 129.5 (C$_{Ar}$); 134.1 (C$_{Ar}$); 135.6 (C$_{Ar}$).

e) Synthesis of diethyl 6-hydroxy-1-diethoxyphosphoryloxy-hexylphosphonate 12

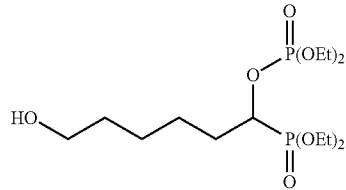

Diethyl 6-hydroxy-1-diethoxyphosphoryloxy-hexylphosphonate 12 was synthesized, from compound 11 (12.0 g, 19.1 mmol), according to the same procedure described for the synthesis of diethyl 10-hydroxy-1-diethoxyphosphoryloxy-decylphosphonate 5. 6.4 g of the desired alcohol 12 were isolated as slightly yellow oil. Yield=86%.

$^1$H NMR (400 MHz, CDCl$_3$): δ=1.26-1.66 (m, 18H, CH$_2$ and POCH$_2$CH$_3$); 1.83-1.95 (m, 2H); 2.28 (1s, 1H, OH); 3.55-3.66 (m, 2H, CH$_2$OH); 4.06-4.22 (m, 8H, POCH$_2$CH$_3$); 4.57-4.68 (m, 1H, CHP). $^{31}$P NMR (162 MHz, CDCl$_3$): δ=-1.0 (d, $^3J_{PP}$=22.1 Hz, CHOP); 20.1 (d, $^3J_{PP}$=22.1 Hz, CHP). $^{13}$C NMR (101 MHz, CDCl$_3$): δ=16.0 (d, $^3J_{CP}$=3.3 Hz, POCH$_2$CH$_3$); 16.1 (d, $^3J_{CP}$=3.2 Hz, POCH$_2$CH$_3$); 16.4 (d, $^3J_{CP}$=5.6 Hz, POCH$_2$CH$_3$); 16.5 (d, $^3J_{CP}$=5.5 Hz, POCH$_2$CH$_3$); 24.5 (d, $^2J_{CP}$=10.9 Hz, CH$_2$CHP); 24.8 (CH$_2$); 30.8 (CH$_2$); 32.3 (CH$_2$); 62.0 (CH$_2$OH); 62.8 (d, $^2J_{CP}$=6.2 Hz, POCH$_2$CH$_3$); 62.9 (d, $^2J_{CP}$=7.1 Hz, POCH$_2$CH$_3$); 64.1 (d, $^2J_{CP}$=5.7 Hz, POCH$_2$CH$_3$); 64.1 (d, $^2J_{CP}$=5.7 Hz, POCH$_2$CH$_3$); 72.7 (dd, $^1J_{CP}$=170.2 Hz, $^2J_{CP}$=7.2 Hz, CHP).

f) Synthesis of diethyl 6-methacryloyloxy-1-diethoxyphosphoryloxy-hexylphosphonate 13

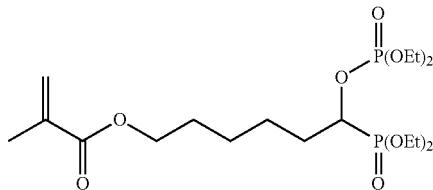

Diethyl 6-methacryloyloxy-1-diethoxyphosphoryloxy-hexylphosphonate 13 was synthesized, from alcohol 12 (3.12 g, 8.0 mmol), according to the same procedure described for the synthesis of diethyl 10-methacryloyloxy-1-diethoxyphosphoryloxy-decylphosphonate 6. 2.84 g of the desired monomer 13 were isolated as slightly yellow oil. Yield=78%.

$^1$H NMR (400 MHz, CDCl$_3$): δ=1.28-1.76 (m, 18H, CH$_2$ and POCH$_2$CH$_3$); 1.81-2.03 (m, 5H, CH$_2$ and CH$_3$); 4.07-4.28 (m, 10H, POCH$_2$CH$_3$ and CH$_2$OCO); 4.57-4.72 (m, 1H, CHP); 5.53-5.59 (m, 1H, CH$_2$=C); 6.10 (1s, 1H, CH$_2$=C). $^{31}$P NMR (162 MHz, CDCl$_3$): δ=-1.1 (d, $^3J_{PP}$=21.8 Hz, CHOP); 19.9 (d, $^3J_{PP}$=21.8 Hz, CHP). $^{13}$C NMR (101 MHz, CDCl$_3$): δ=16.0 (d, $^3J_{CP}$=4.9 Hz, POCH$_2$CH$_3$); 16.1 (d, $^3J_{CP}$=4.8 Hz, POCH$_2$CH$_3$); 16.4 (d, $^3J_{CP}$=5.8 Hz, POCH$_2$CH$_3$); 16.5 (d, $^3J_{CP}$=5.6 Hz, POCH$_2$CH$_3$); 18.3 (CH$_3$); 25.0 (d, $^2J_{CP}$=10.5 Hz, CH$_2$CHP); 25.7 (CH$_2$); 28.4

(CH$_2$); 30.9 (CH$_2$); 62.8 (d, $^2J_{CP}$=6.7 Hz, POCH$_2$CH$_3$); 64.0 (d, $^2J_{CP}$=5.9 Hz, POCH$_2$CH$_3$); 64.5 (CH$_2$OCO); 73.0 (dd, $^1J_{CP}$=169.9 Hz, $^2J_{CP}$=7.3 Hz, CHP); 125.3 (CH$_2$=C); 136.4 (CH$_2$=C); 167.5 (C=O).

g) Synthesis of 6-methacryloyloxy-1-dihydroxyphosphoryloxy-hexylphosphonic acid 14

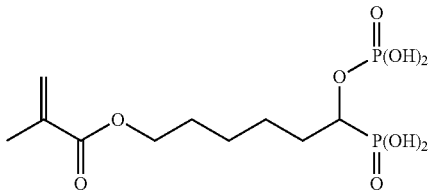

6-Methacryloyloxy-1-dihydroxyphosphoryloxy-hexylphosphonic acid 14 was synthesized, from monomer 13 (2.75 g, 6.0 mmol), according to the same procedure described for the synthesis of 10-methacryloyloxy-1-dihydroxyphosphoryloxy-decylphosphonic acid 7. 1.96 g of the desired monomer 14 were isolated as a highly viscous yellow oil. Yield=95%.

$^1$H NMR (400 MHz, MeOD): δ=1.28-1.78 (m, 6H, CH$_2$); 1.79-1.98 (m, 5H, CH$_2$ and CH$_3$); 4.15 (t, $^3J_{HH}$ 6.6 Hz, 2H, CH$_2$OCO); 4.36-4.48 (m, 1H, CHP); 5.59-5.63 (m, 1H, CH$_2$=C); 6.08 (1s, 1H, CH$_2$=C). $^{31}$P NMR (162 MHz, MeOD): δ=0.3 (d, $^3J_{PP}$=18.8 Hz, CHOP); 19.3 (d, $^3J_{PP}$=18.8 Hz, CHP). $^{13}$C NMR (101 MHz, MeOD): δ=17.0 (CH$_3$); 24.7 (d, $^2J_{CP}$=10.3 Hz, CH$_2$CHP); 25.4 (CH$_2$); 28.1 (CH$_2$); 30.6 (CH$_2$); 64.4 (CH$_2$OCO); 73.0 (dd, $^1J_{CP}$=166.1 Hz, $^2J_{CP}$=7.2 Hz, CHP); 124.6 (CH$_2$=C); 136.5 (CH$_2$=C); 167.5 (C=O).

Example 3

Synthesis of 6-[(2-methacryloyloxyethylamino)carbonyloxy]-1-(dihydroxyphosphoryloxy)-hexylphosphonic acid 16 a) Synthesis of Diethyl 6-[(2-methacryloyloxyethylamino)-carbonyloxy]-1-(diethoxyphosphoryloxy)-hexylphosphonate 15

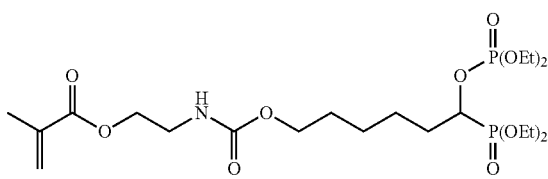

A solution of dibutyltin dilaurate (25.5 mg, 0.041 mmol) in anhydrous DCM (2.0 mL) was added, under argon atmosphere, to a solution of diethyl 6-hydroxy-1-diethoxyphosphoryloxy-hexylphosphonate 12 (3.15 g, 8.1 mmol) in anhydrous DCM (10.0 mL). 2-isocyanatoethyl methacrylate (1.14 mL, 8.1 mmol) was subsequently added dropwise to the mixture. The solution was stirred for 3 h at RT and concentrated under reduced pressure. The crude product was purified by flash column chromatography (eluent: ethyl acetate/methanol: 9/1). 4.3 g of the desired compound were isolated. Yield: 93%.

$^1$H NMR (400 MHz, CDCl$_3$): δ=1.28-1.74 (m, 18H, CH$_2$ and POCH$_2$CH$_3$); 1.80-1.98 (m, 5H, CH$_2$ and CH$_3$); 3.40-3.54 (m, 2H, CH$_2$NH); 4.00-4.26 (m, 12H, POCH$_2$CH$_3$, CH$_2$OCONH and CH$_2$OCO); 4.56-4.67 (m, 1H, CHP); 5.24 (s, 1H, NH); 5.57-5.61 (m, 1H, CH$_2$=C); 6.13 (1s, 1H, CH$_2$=C). $^{31}$P NMR (162 MHz, CDCl$_3$): δ=−1.1 (d, $^3J_{PP}$=22.2 Hz, CHOP); 20.1 (d, $^3J_{PP}$=22.2 Hz, CHP). $^{13}$C NMR (101 MHz, CDCl$_3$): δ=16.0 (d, $^3J_{CP}$=4.6 Hz, POCH$_2$CH$_3$); 16.1 (d, $^3J_{CP}$=4.4 Hz, POCH$_2$CH$_3$); 16.4 (d, $^3J_{CP}$=5.8 Hz, POCH$_2$CH$_3$); 16.5 (d, $^3J_{CP}$=5.8 Hz, POCH$_2$CH$_3$); 18.3 (CH$_3$); 25.0 (d, $^2J_{CP}$=10.5 Hz, CH$_2$CHP); 25.7 (CH$_2$); 28.5 (CH$_2$); 30.8 (CH$_2$); 40.0 (CH$_2$NH); 62.8 (d, $^2J_{CP}$=6.1 Hz, POCH$_2$CH$_3$); 62.8 (d, $^2J_{CP}$=7.2 Hz, POCH$_2$CH$_3$); 63.8 (CH$_2$OCO); 64.1 (d, $^2J_{CP}$=6.1 Hz, POCH$_2$CH$_3$); 65.0 (CH$_2$OCO); 73.0 (dd, $^1J_{CP}$=169.9 Hz, $^2J_{CP}$=7.3 Hz, CHP); 126.0 (CH$_2$=C); 136.0 (CH$_2$=C); 156.7 (C=O); 167.2 (C=O).

b) Synthesis of 6-[(2-methacryloyloxyethylamino)-carbonyloxy]-1-(dihydroxyphosphoryloxy)-hexylphosphonic acid 16

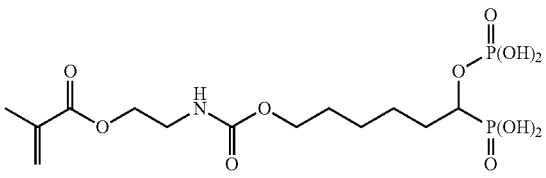

6-[(2-methacryloyloxyethylamino)-carbonyloxy]-1-(dihydroxyphosphoryloxy)-hexylphosphonic acid 16 was synthesized, from monomer 15 (1.0 g, 1.83 mmol), according to the same procedure described for the synthesis of 10-methacryloyloxy-1-dihydroxyphosphoryloxy-decylphosphonic acid 7. 750 mg of the desired monomer 16 were isolated as a highly viscous yellow oil. Yield=94%.

$^1$H NMR (400 MHz, MeOD): δ=1.26-1.74 (m, 6H, CH$_2$); 1.77-1.97 (m, 5H, CH$_2$ and CH$_3$); 3.38 (t, $^3J_{HH}$=5.5 Hz, 2H, CH$_2$NH); 4.03 (t, $^3J_{HH}$=6.5 Hz, 2H, CH$_2$OCO); 4.17 (t, $^3J_{HH}$=5.5 Hz, 2H, CH$_2$OCONH); 4.34-4.47 (m, 1H, CHP); 5.61-5.65 (m, 1H, CH$_2$=C); 6.11 (1s, 1H, CH$_2$=C). $^{31}$P NMR (162 MHz, MeOD): δ=0.3 (CHOP); 19.3 (CHP). $^{13}$C NMR (101 MHz, MeOD): δ=17.0 (CH$_3$); 24.8 (d, $^2J_{CP}$=10.4 Hz, CH$_2$CHP); 25.3 (CH$_2$); 28.6 (CH$_2$); 30.6 (CH$_2$); 39.3 (CH$_2$NH); 63.2 (CH$_2$OCO); 64.5 (CH$_2$OCO); 73.0 (dd, $^1J_{CP}$=166.0 Hz, $^2J_{CP}$=7.2 Hz, CHP); 125.1 (CH$_2$=C); 136.2 (CH$_2$=C); 157.9 (C=O); 167.3 (C=O).

Example 4

Synthesis of 10-(methacryloyloxy)-decylbisphosphonic acid 17

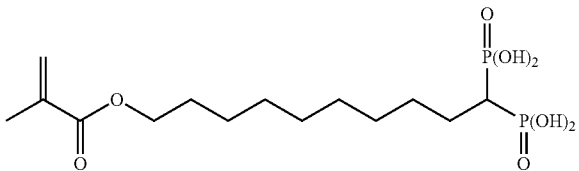

This bisphosphonic acid 17 was synthesized, in 6 steps, according to a procedure similar to the one described in the literature for the synthesis of the 6-(methacryloyloxy)-hexylbisphosphonic acid (Catel, Y. et al., *Eur. Polym. J.* 2012, 48, 318-330).

$^1$H NMR (400 MHz, MeOD): δ=1.26-1.45 (m, 10H, CH$_2$); 1.54-1.73 (m, 4H, CH$_2$); 1.82-2.00 (m, 5H, CH$_2$ and CH$_3$); 2.16 (tt, $^2J_{HP}$=23.6 Hz, $^3J_{HH}$=6.1 Hz, 1H, CHP$_2$); 4.13 (t, $^3J_{HH}$=6.6 Hz, 2H, CH$_2$OCO); 5.58-5.62 (m, 1H, CH$_2$=C); 6.07 (1s, 1H, CH$_2$=C). $^{31}$P NMR (162 MHz, MeOD): δ=22.7. $^{13}$C NMR (101 MHz, MeOD): δ=17.0 (CH$_3$); 25.3 (t, $^2J_{CP}$=4.8 Hz, CH$_2$CHP); 25.7 (CH$_2$); 28.3 (CH$_2$); 28.9 (CH$_2$); 29.0 (CH$_2$); 29.1 (t, $^3J_{CP}$=6.7 Hz, CH$_2$CH$_2$CHP); 29.2 (CH$_2$); 64.4 (CH$_2$OCO); 73.0 (dd, $^1J_{CP}$=166.1 Hz, $^2J_{CP}$=7.2 Hz, CHP); 124.6 (CH$_2$=C); 136.5 (CH$_2$=C); 167.5 (C=O).

Example 5

Investigation of the Photopolymerization of 10-methacryloyloxy-1-dihydroxyphosphoryloxy-decylphosphonic acid 7 by Means of DSC 0.5 mol.-% of the photoinitiator bis(4-methoxybenzoyl) diethylgermanium was added to a mixture of 2-hydroxyethyl methacrylate (HEMA) and monomer 7 in the molar ratio of 8:2. The mixture was polymerized in a differential scanning calorimeter (Diamond, Perkin Elmer). The mixture was irradiated with a LED lamp (Bluephase, Ivoclar Vivadent) for 2 min at 37° C. 10-(Methacryloyloxy)decylphosphonic acid (MDPA) and 10-(methacryloyloxy)decyl dihydrogen phosphate (MDP) were also copolymerized with HEMA using the same conditions. FIG. 1 shows the rate of polymerization (R$_p$) of the different mixtures as a function of time. The results clearly show that new monomer 7 is significantly more reactive than the corresponding dihydrogen phosphate MDP and the corresponding phosphonic acid MDPA.

Example 6

Adhesive Properties of Selected Acidic Hybrid Monomers

To investigate the adhesion to dentin and enamel on bovine teeth, self-etch adhesives (SEAs) having the composition shown in Table 1 were prepared. Formulations based on hybrid acidic monomers 7, 14 and 16 as well as on bisphosphonic acid 17, MDP and MDPA were prepared. Freshly extracted bovine mandibular incisors were embedded in unsaturated polyester resin (Castolite). Flat dentinal and enamel surfaces were prepared with 120-grit and 400-grit wet silicon carbide paper on the labial side of the embedded teeth. light cured for 10 s with a LED curing light (Bluephase The adhesive was first rubbed on the prepared surface (dentin or enamel) with a microbrush for 20 s. The adhesive layer was strongly air dried and G20, Ivoclar Vivadent AG). A 3-mm thick cylindrical Teflon mold with a central 2-mm diameter circular hole was fixed on the surface. A composite (Tetric EvoCeram, Ivoclar Vivadent AG) was inserted into the mold and light-cured for 20 s. The samples were finally stored in water at 37° C. for 24 h before being tested. The shear bond strength was determined in accordance with the ISO guideline "ISO 2003-ISO TR 11405: Dental Materials Guidance on Testing of Adhesion to Tooth Structure". The results are given in Table 2. SEAs based on the new acidic hybrid monomers 7, 14 and 16 led to significantly higher dentin SBS than the adhesives containing the phosphonic acid MDPA or the dihydrogen phosphate MDP. SEAs based on monomers 7, 14 and 16 also provided significantly higher enamel SBS than SEAs containing MDPA or bisphosphonic acid 17.

TABLE 1

Composition of the adhesives A-F (data in % by weight)

| Component | A | B | C | D*) | E*) | F*) |
|---|---|---|---|---|---|---|
| 7 | 15.00 | — | — | — | — | — |
| 14 | — | 15.00 | — | — | — | — |
| 16 | — | — | 15.00 | — | — | — |
| 17 | — | — | — | 15.00 | — | — |
| MDPA[4)] | — | — | — | — | 15.00 | — |
| MDP[5)] | — | — | — | — | — | 15.00 |
| Bis-GMA[1)] | 22.40 | 22.40 | 22.40 | 22.40 | 22.40 | 22.40 |
| DEBAP[2)] | 40.00 | 40.00 | 40.00 | 40.00 | 40.00 | 40.00 |
| Photoinitiator[3)] | 2.57 | 2.57 | 2.57 | 2.57 | 2.57 | 2.57 |
| Deionized water | 15.00 | 15.00 | 15.00 | 15.00 | 15.00 | 15.00 |
| Isopropanol | 5.00 | 5.00 | 5.00 | 5.00 | 5.00 | 5.00 |
| BHT | 0.03 | 0.03 | 0.03 | 0.03 | 0.03 | 0.03 |

*)comparative example
[1)]Addition product of methacrylic acid and bisphenol A diglycidyl ether
[2)]N,N'-diethyl-1,3-bis-(acrylamido)propane
[3)]Mixture of camphorquinone (0.9%), 4-dimethylbenzoic acid ethyl ester (0.42%) and the acylphosphine oxide Lucerin TPO (BASF; 1.25%)
[4)]10-(methacryloyloxy)decylphosphonic acid
[5)]10-(methacryloyloxy)decyl dihydrogen phosphate

TABLE 2

Dentin and enamel shear bond strength (SBS) of the adhesives A-F

| Adhesive | Dentin SBS (MPa) | Enamel SBS (MPa) |
|---|---|---|
| A | 36.5 ± 4.1 | 25.8 ± 2.8 |
| B | 37.3 ± 5.1 | 29.1 ± 4.5 |
| C | 38.5 ± 3.8 | 29.8 ± 3.0 |
| D*) | 34.9 ± 4.9 | 17.6 ± 2.8 |
| E*) | 22.0 ± 3.3 | 16.4 ± 2.8 |
| F*) | 27.7 ± 4.8 | 22.6 ± 4.0 |

*)comparative example

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:
1. Acidic monomer according to Formula I:

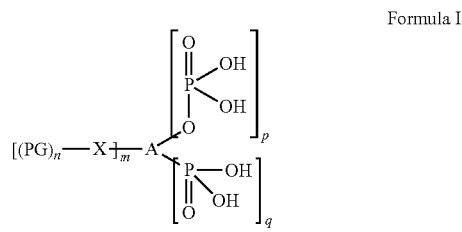

Formula I in which
A=a linear or branched aliphatic C$_1$-C$_{18}$-hydrocarbon group, which can be interrupted by one or more —O—, —S—, —CO—O—, —O—CO—NH—, —HN—CO—NH— or —CO—NR$^1$—,
R$^1$=H or a C$_1$-C$_6$ alkyl group,
X=is absent or is a linear or branched aliphatic C$_1$-C$_{10}$ hydrocarbon group, which can be interrupted by one or more —O—, —S—, —CO—O—, —O—CO—NH—, —HN—CO—NH— or —CO—NR$^2$—, R$^2$=H or a C$_1$-C$_6$ alkyl group, PG=a radically polymerizable group selected from vinyl, allyl, CH$_2$=CR$^3$—CO—Y— or R$^4$O—CO—C(=CH$_2$)—CH$_2$—Y—, Y=O or NR$^5$ or is absent, R$^3$=H or CH$_3$ R$^4$=H or a C$_1$-C$_7$ alkyl group, R$^5$=H or a C$_1$-C$_7$ alkyl group, n=1, 2, 3 or 4, m=1 or 2, p=1, 2 or 3, and q=1, 2 or 3.

2. The acidic monomer of claim 1, wherein the variables of Formula I have the following meanings:

A=linear or branched C$_1$-C$_{10}$ aliphatic group, which can be interrupted by one or more —O—, —S—, —CO—O—, —O—CO—NH—, —HN—CO—NH— or —CO—NR$^1$—,

R$^1$=H,

X=—CH$_2$— or absent,

PG=CH$_2$=CR$^3$—CO—Y—,

Y=O or NR$^5$,

R$^3$=H or CH$_3$,

R$^5$=H or a C$_1$-C$_4$ alkyl group n=1 or 2, m=1, p=1, and q=1.

3. The acidic monomer of claim 2, wherein the variables of Formula I have the following meanings:

A=linear or branched C$_3$-C$_{10}$ aliphatic group, which can be interrupted by one —O—, —S—, —CO—O—, —O—CO—NH—, —HN—CO—NH— or —CO—NR$^1$—,

R$^1$=H,

X=absent,

PG=CH$_2$=CR$^3$—CO—Y—,

Y=O or NR$^5$,

R$^3$=H or CH$_3$,

R$^5$=H or a C$_1$-C$_3$ alkyl group n=1 or 2, m=1, p=1, q=1.

4. The acidic monomer of claim 2, wherein the dihydrogen phosphate group —O—PO(OH)$_2$ and the phosphonic acid group —PO(OH)$_2$ are bound to the same carbon atom.

5. Dental material which comprises at least one acidic monomer according to claim 1.

6. The dental material of claim 5, which comprises 0.1 to 50 wt.-% of the acidic monomer according to Formula I, based on the total weight of the dental material.

7. The dental material of claim 5, which comprises 1 and 20 wt.-% of the acidic monomer according to Formula I, based on the total weight of the dental material.

8. The dental material of claim 5 which comprises at least one additional radically polymerizable monomer and also at least one initiator for the radical polymerization.

9. The dental material of claim 8, which comprises at least one multifunctional (meth)acrylate or a mixture of mono- and multifunctional (meth)acrylates.

10. The dental material of claim 5, which comprises at least one filler.

11. The dental material of claim 5, which comprises a) 0.1 to 50 wt.-% of acidic monomer(s) of general formula I, b) 0.01 to 10 wt.-% of initiator(s), c) 5 to 80 wt.-% of additional monomer(s), d) 0 to 80 wt.-% of filler(s), e) 0 to 70 wt.-% of solvent(s), and optionally f) 0.01 to 10 wt.-% of further additive(s), in each case relative to the total mass of the dental material.

12. The dental material of claim 5, which comprises a) 1 to 35 wt.-% of acidic monomer(s) of general formula I, b) 0.1 to 3.0 wt.-% of initiator(s), c) 5 to 60 wt.-% of additional monomer(s), d) 0 to 80 wt.-% of filler(s), e) 0 to 50 wt.-% of solvent(s), and optionally f) 0.01 to 3 wt.-% of further additive(s), in each case relative to the total mass of the dental material.

13. The dental material of claim 5, which comprises a) 1 to 20 wt.-% of acidic monomer(s) of general formula I, b) 0.1 to 3.0 wt.-% of initiator(s), c) 5 to 60 wt.-% of additional monomer(s), d) 0 to 80 wt.-% of filler(s), e) 0 to 25 wt.-% of solvent(s), and optionally f) 0.01 to 3 wt.-% of further additive(s), in each case relative to the total mass of the dental material.

14. The dental material of claim 11 for use as an adhesive, which comprises a) 0.1 to 50 wt.-% of acidic monomer(s) of general formula I, b) 0.01 to 10 wt.-% of initiator(s), c) 10 to 70 wt.-% of additional monomer(s), d) 0 to 20 wt.-% of filler(s), e) 5 to 50 wt.-% of solvent(s), and optionally f) 0.01 to 3 wt.-% of further additive(s), in each case relative to the total mass of the dental material.

15. The dental material of claim 14 wherein the solvent(s) comprises water or a mixture of water, ethanol and/or acetone.

16. The dental material of claim 11 for use as an adhesive, which comprises a) 1 to 35 wt.-% of acidic monomer(s) of general formula I, b) 0.1 to 3.0 wt.-% of initiator(s), c) 10 to 40 wt.-% of additional monomer(s), d) 0 to 20 wt.-% of filler(s), e) 5 to 40 wt.-% of solvent(s), and optionally f) 0.01 to 3 wt.-% of further additive(s), in each case relative to the total mass of the dental material.

17. The dental material of claim 11 for use as an adhesive, which comprises a) 1 to 20 wt.-% of acidic monomer(s) of general formula I, b) 0.1 to 3.0 wt.-% of initiator(s), c) 10 to 40 wt.-% of additional monomer(s), d) 0 to 20 wt.-% of filler(s), e) 5 to 30 wt.-% of solvent(s), and optionally f) 0.01 to 3 wt.-% of further additive(s), in each case relative to the total mass of the dental material.

18. The dental material of claim 11 for use as a cement, which comprises a) 0.1 to 50 wt.-% of acidic monomer(s) of general formula I, b) 0.01 to 10 wt.-% of initiator(s),
c) 10 to 70 wt.-% of additional monomer(s),
d) 30 to 75 wt.-% of filler(s),
e) 0 to 5 wt.-% of solvent(s),
f) 0.01 to 3 wt.-% of further additives,
in each case relative to the total mass of the dental material.

19. The dental material of claim 11 for use as a cement, which comprises
a) 1 to 35 wt.-% of acidic monomer(s) of general formula I,
b) 0.1 to 3.0 wt.-% of initiator(s),
c) 10 to 40 wt.-% of additional monomer(s),
d) 30 to 75 wt.-% of filler(s),
e) less than 1 wt.-% of solvent(s),
f) 0.01 to 3 wt.-% of further additives,
in each case relative to the total mass of the dental material.

20. The dental material of claim 11 for use as a cement, which comprises
a) 1 to 20 wt.-% of acidic monomer(s) of general formula I,
b) 0.1 to 3.0 wt.-% of initiator(s),
c) 10 to 40 wt.-% of additional monomer(s),
d) 30 to 75 wt.-% of filler(s),
e) less than 1 wt.-% of solvent(s),
f) 0.01 to 3 wt.-% of further additives,
in each case relative to the total mass of the dental material.

21. The dental material of claim 5 for intraoral use to restore damaged teeth.

22. The dental material of claim 21 for use as dental cement, filling composite, veneering or blending material.

* * * * *